US010136958B2

(12) United States Patent
Csernatoni

(10) Patent No.: US 10,136,958 B2
(45) Date of Patent: Nov. 27, 2018

(54) TISSUE PROTECTOR AND METHOD OF USE

(71) Applicant: Zsolt Csernatoni, Woodstock, GA (US)

(72) Inventor: Zsolt Csernatoni, Woodstock, GA (US)

(73) Assignee: Amendia, Inc., Marietta, GA (US)

( * ) Notice: Subject to any disclaimer, the term of this patent is extended or adjusted under 35 U.S.C. 154(b) by 586 days.

(21) Appl. No.: 14/525,880

(22) Filed: Oct. 28, 2014

(65) Prior Publication Data

US 2016/0113717 A1    Apr. 28, 2016

(51) Int. Cl.
| | | |
|---|---|---|
| *A61B 17/00* | (2006.01) | |
| *A61B 17/02* | (2006.01) | |
| *A61B 46/27* | (2016.01) | |
| *A61F 2/46* | (2006.01) | |
| *A61B 90/00* | (2016.01) | |

(52) U.S. Cl.
CPC .......... *A61B 46/27* (2016.02); *A61B 17/0218* (2013.01); *A61B 2017/00862* (2013.01); *A61B 2017/0212* (2013.01); *A61B 2017/0225* (2013.01); *A61B 2017/0262* (2013.01); *A61B 2090/08021* (2016.02); *A61F 2/4611* (2013.01)

(58) Field of Classification Search
CPC .. A61B 2090/08021; A61B 2017/0225; A61B 17/0218; A61B 17/3417; A61B 17/3468; A61M 2025/0024; A61M 2025/0025; A61M 25/0041; A61F 2/46

See application file for complete search history.

(56) References Cited

U.S. PATENT DOCUMENTS

| | | | | |
|---|---|---|---|---|
| 4,984,564 A | * | 1/1991 | Yuen ................. | A61B 17/0293 600/207 |
| 5,308,327 A | * | 5/1994 | Heaven ............ | A61B 17/00234 604/103.09 |
| 6,205,361 B1 | * | 3/2001 | Kuzma ................... | A61N 1/05 607/116 |
| 6,896,680 B2 | | 5/2005 | Michelson | |
| 7,211,085 B2 | | 5/2007 | Michelson | |
| 7,377,930 B2 | | 5/2008 | Loughran | |
| 7,951,110 B2 | | 5/2011 | Bishop et al. | |
| 7,998,143 B2 | | 8/2011 | Michelson | |
| 2005/0137668 A1 | * | 6/2005 | Khan ................. | A61N 1/0553 607/118 |
| 2006/0217754 A1 | | 9/2006 | Boehm et al. | |
| 2008/0051817 A1 | * | 2/2008 | Leahy ............... | A61B 17/0218 606/191 |
| 2009/0093821 A1 | * | 4/2009 | Edmundson ....... | A61B 17/3421 606/108 |

(Continued)

FOREIGN PATENT DOCUMENTS

GB    1524528    9/1978

*Primary Examiner* — David W Bates
(74) *Attorney, Agent, or Firm* — David L. King

(57) ABSTRACT

A tissue protector has a body structure having a longitudinal extending thin web. The body structure has an unconstrained first shape configured to form a nerve shield and is configured to shrink about a longitudinal axis to a smaller constrained second shape sized to fit into a lumen of a cannula. Preferably, the second constrained shape is oval or round having a maximum diameter equal or less than an inside diameter of the lumen. The body structure is configured to return to the first shape when the cannula is withdrawn or returned to this shape as the implant advances.

10 Claims, 7 Drawing Sheets

(56) References Cited

U.S. PATENT DOCUMENTS

| | | | |
|---|---|---|---|
| 2010/0087713 A1* | 4/2010 | Eliash | A61B 17/02 600/206 |
| 2014/0114133 A1* | 4/2014 | Tally | A61B 17/88 600/203 |
| 2016/0038131 A1* | 2/2016 | White | A61B 17/320016 606/90 |

* cited by examiner

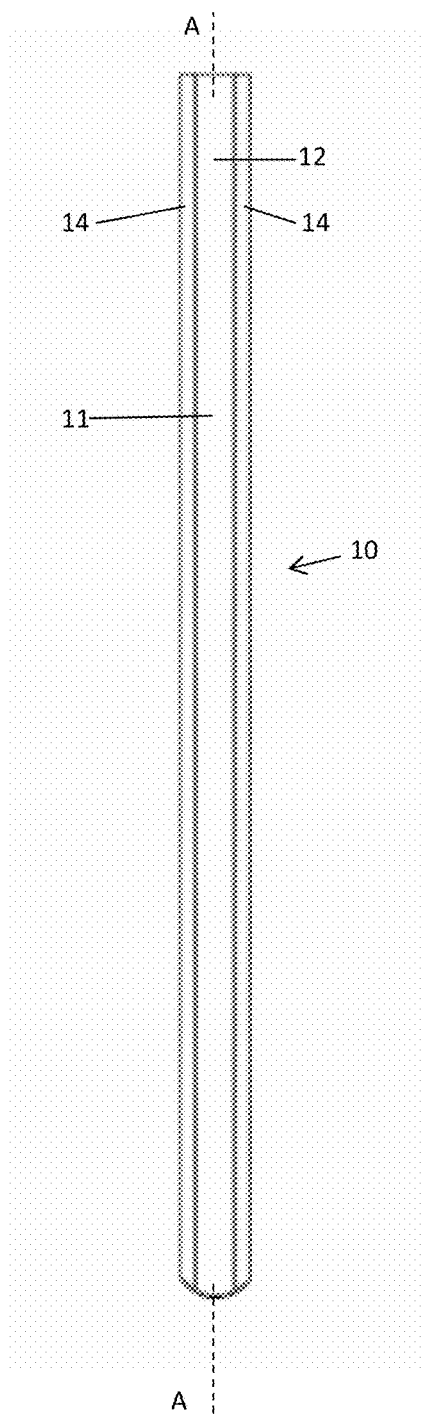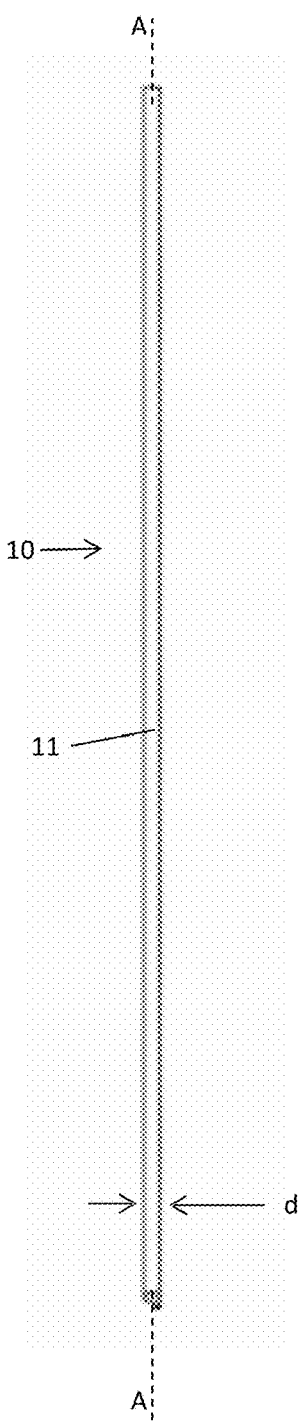
FIG. 3
FIG. 4

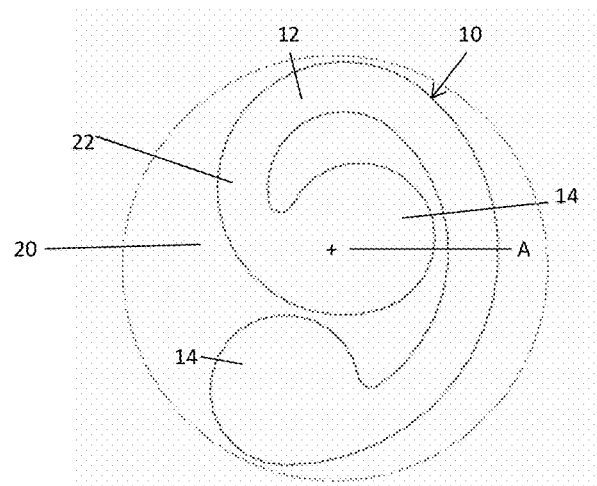
FIG. 5
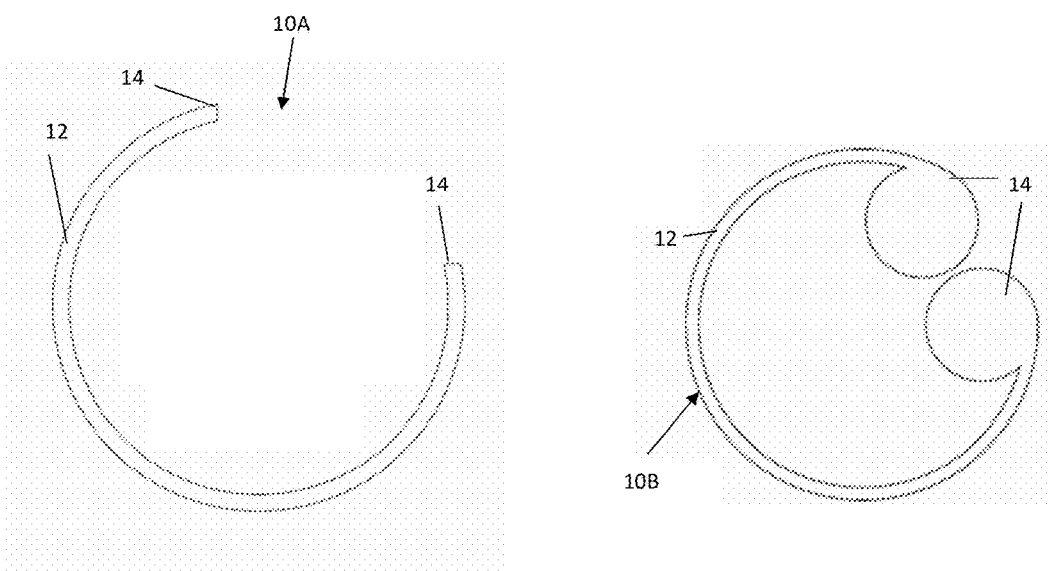
FIG. 6A
FIG. 6C

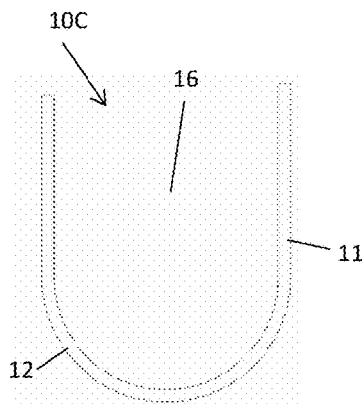
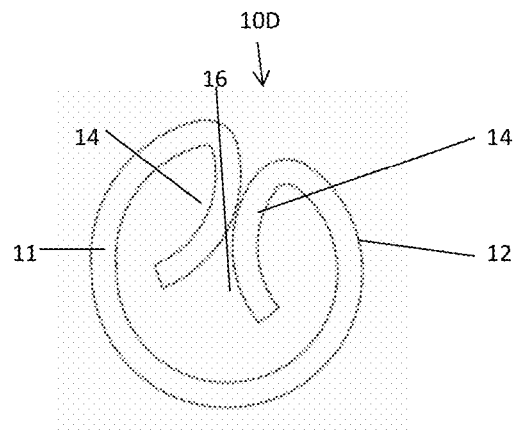
FIG. 9A             FIG. 9B
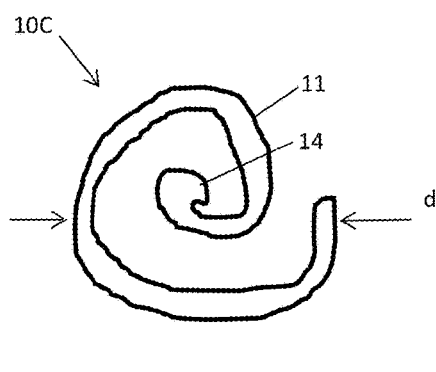
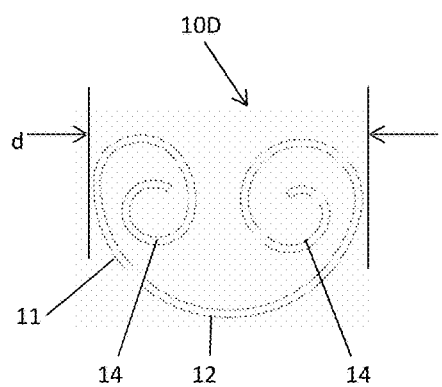
FIG. 9C             FIG. 9D

TISSUE PROTECTOR AND METHOD OF USE

TECHNICAL FIELD

The present invention relates to a tissue protector, or in this particular example, a tissue and nerve shield for use in minimally invasive spinal surgery.

BACKGROUND OF THE INVENTION

When a surgeon is accessing a region to be repaired such as the disc space between adjacent vertebrae, great care must be taken to avoid injury to the exposed nerve root.

Dural tears, nerve root damage, bleeding and infection, operating on the wrong level or on the wrong side are as real issues in all spinal surgeries.

With thoracic approaches, pneumothorax is also a possibility.

In addition, some injuries may be underestimated or even go unnoticed, such as a dural tear under the low-pressure irrigation.

It is an objective of the present invention to further minimize the potential for such complications by providing a unique protective tissue protector or nerve shield made in accordance to the invention as disclosed herein.

SUMMARY OF THE INVENTION

A tissue protector or nerve shield has a body structure having a longitudinal extending thin web. The body structure has an unconstrained first shape configured to form a nerve shield and is configured to shrink about a longitudinal axis to a smaller constrained second shape sized to fit into a lumen of a cannula. Preferably, the second constrained shape is oval or round having a maximum diameter equal or less than an inside diameter of the lumen. The body structure is configured to return to the first shape when the cannula is withdrawn from between two adjacent vertebral bodies and the body structure is held in position between the vertebral bodies.

The web is configured to shield a nerve root and the surrounding tissue. Also, the unconstrained first shape of the web is sized of a constant width to receive a spinal implant for insertion between the two vertebral bodies. The web forms a guide and a shield for the spinal implant. The web can have a thin oval or circular cross section in the unconstrained first shape. Alternatively, the web can have a channel or "U" cross section, rectangular or triangular cross section in the unconstrained first shape.

In a preferred embodiment, the body structure further has a first proximal end and a second distal end with the longitudinal extending thin flexible web with a pair of solid rails on each lateral side of the web between said ends, the web being interposed between said rails. The rails are parallel extending the entire length of the body structure. The nerve shield when unconstrained has at least one rail shielding a nerve root. The rails are spaced by the constant width web, when the body structure is in the unconstrained first shape, a constant lateral distance or width to form a shallow channel to receive a spinal implant or surgical instrument. The pair of rails is configured to guide a spinal implant during insertion while at least one of said rails shields the nerve root or tissue of interest. The rails are enlarged longitudinally extending projections having a round or at least partially round cross section. The web can be a thin rectangular cross section in the unconstrained first shape.

The invention permits a method of shielding a nerve root or tissue of interest during a spinal surgical procedure having the steps of: making an incision; inserting a cannula, wherein the cannula has a shield constrained inside the lumen of the cannula; positioning the distal end of the cannula past or beside a nerve root or tissue; withdrawing the cannula while holding the shield in position past or beside the nerve root or tissue; and freeing the shield allowing movement from a constrained shape to an unconstrained shape to protect and shield the nerve root or tissue. The method further can include inserting a spinal implant at the proximal end using the unconstrained shield as a guide to position the implant between two vertebral bodies at the distal end.

BRIEF DESCRIPTION OF THE DRAWINGS

The invention will be described by way of example and with reference to the accompanying drawings in which:

FIG. 3 is an exemplary frontal view of the device in a deployed first shape.

FIG. 4 is a frontal view of the rolled or wrapped tissue protector showing a second constrained shape for insertion in a lumen of a cannula.

FIG. 5 is a top view of the nerve shield of FIG. 4 in a second constrained shape, the circular dashed lines representing the diameter of a lumen of a cannula into which the device can fit.

FIG. 6A shows a first alternative embodiment end view of the device showing no rails.

FIG. 6C shows a second alternative embodiment showing rails with an oval web, both devices shown in an unconstrained first shape.

FIG. 9A is a third alternative embodiment showing a "U" shape configuration unconstrained.

FIG. 9B is the constrained view of the third alternative.

FIG. 9C is a fourth view of an alternative embodiment.

FIG. 9D is the constrained view of the fourth alternative.

DETAILED DESCRIPTION OF THE INVENTION

Figure 1:
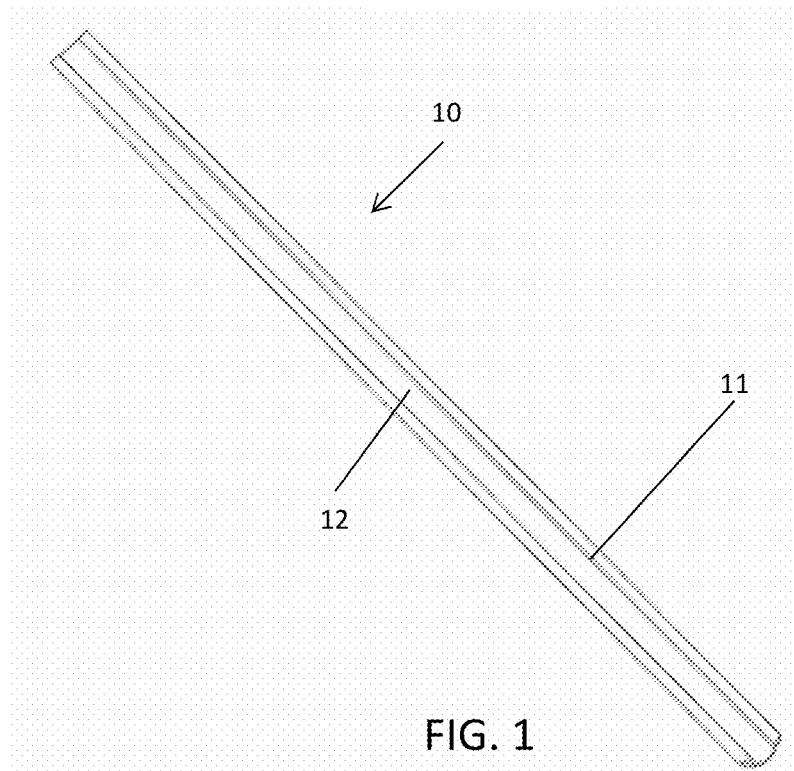
FIG. 1 is a perspective view of a nerve shield of a first embodiment of the present invention shown in a deployed first unconstrained shape.
Figure 2:
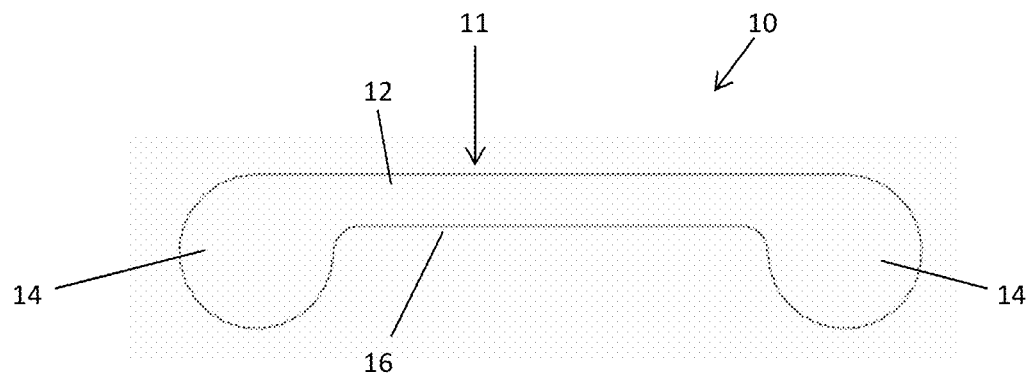
FIG. 2 is a top view showing the end of the deployed shield.

With reference to the drawings FIGS. 1 and 2, a unique tissue protector 10 is illustrated. The tissue protector 10 has a first unconstrained shape having a size typically much larger than an 8.5 mm lumened cannula as shown by the cross sectional circle. Such cannulas are often used in spinal surgery where minimally invasive approach is taken where an incision is cut into the patient's back above a target area of the spine and the cannula is inserted. The cannula provides an access port into which tools can go in and clean out the disc space and provide a prepared surface into which a spinal implant 100 can be inserted. Ideally, the insertion of a spinal implant 100 should be conducted in such a fashion that the nerve root is protected during the insertion procedure. In order to accomplish this, the present invention provides a tissue protector 10 that can lay adjacent one side of the nerve root and provide a barrier between the spinal implant 100 and the nerve root or any tissue along the way.

Figure 6B:
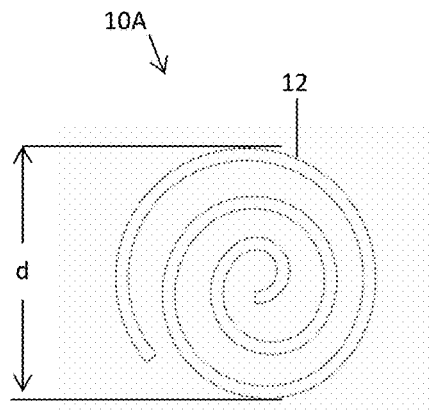
FIG. 6B shows the end of FIG. 6A in the constrained second shape.
Figure 6D:
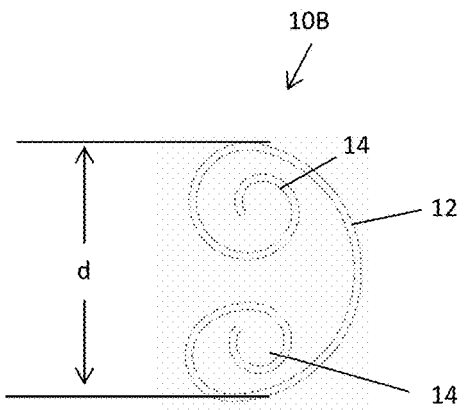
FIG. 6D shows the end of FIG. 6C in the constrained second shape.

A unique feature of the present invention tissue protector 10 is that it is provided with a very thin web 12 as shown in FIG. 2. The web 12, shown in FIGS. 1 and 3, extends longitudinally down the length of the tissue protector 10 in an unconstrained first shape. It is designed to be wrapped or rolled about a longitudinal axis A into a tightly compressed size sufficiently small to fit inside the lumen 22 of a small diameter cannula 20, as shown in FIGS. 4 and 5. The tissue protector 10 can take a variety of cross sectional shapes as shown in FIGS. 5, 6A, 6B, 6C, 6D, 9A and 9C. The web 12 is shown as a continuous piece of thin material having an almost fully circular shape, but open forming two ends 14 such that the web 12 can be spirally wound to compress it to a diameter d that is smaller than the lumen opening of a cannula 20 into which it will be inserted. Alternatively, shown in FIG. 6C, is an embodiment having a cross sectional shape wherein two enlarged projections or bulbous ends 14 are provided and these ends 14 similarly can be folded inwardly to achieve the diameter d as required, as shown in FIG. 6D. Both of these designs are such that when positioned inside a cannula 20, they can be easily held in that position when the cannula 20 is positioned into a target region. The distal end of the cannula 20 will reach at or past the nerve root and in doing so the shield 10 which is carried inside the cannula 20 can be held in at the target location as the cannula 20 is withdrawn from the incision leaving only the tissue protector 10 in place adjacent the nerve root. The tissue protector 10, being free of the cannula 20, returns to the unconstrained first shape. When this occurs, a spinal implant 100 can be used to be slid down the interior surface of the tissue protector 10.

Figure 8:
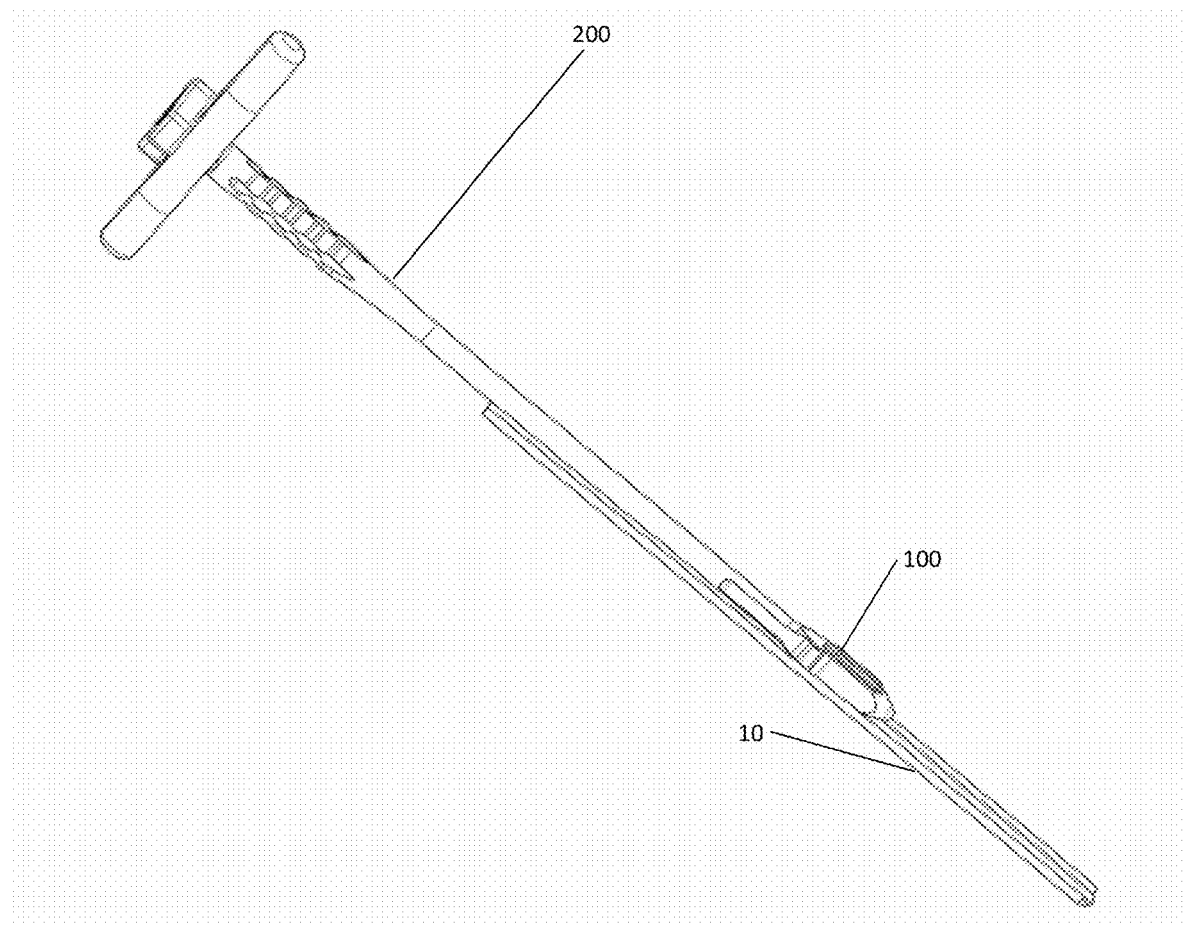
FIG. 8 is a perspective view of the nerve shield used as a guide for insertion of a spinal implant.

With reference to FIGS. 1-5, a preferred embodiment of the present invention is illustrated. This preferred embodiment tissue protector 10 of the present invention has the web 12 as a straight or flat rectangular thin material extending longitudinally wherein the ends have two enlarged bulbous features or projections 14 that are parallel and positioned at a lateral distance creating a space between the enlarged ends forming a shallow channel 16. As shown in FIGS. 2 and 3, the unconstrained shape has a fairly large width. This width can be as high as 16 mm. However, as shown in FIG. 4, when the shield body structure 11 is folded or wrapped or rolled about a longitudinal axis A into a tightly constrained second shape, the nerve shield 10 occupies a space which will fit within an 8.5 mm diameter lumen of a cannula 20. This is fully illustrated in FIG. 5. When in this constrained second position, the tissue protector 10 can be positioned inside a cannula 20 and can be held there until the cannula 20 is positioned in the proper location or target region between two adjacent vertebral bodies in the disc space at or past the nerve root. At this point, the cannula 20 can be withdrawn while holding the tissue protector 10 into position at the location. As the tissue protector 10 is freed from the constraint of being inside lumen 22 of the cannula 20 it is free to regain its unconstrained first shape. When the tissue protector 10 is fully deployed free of the cannula 20, it achieves the appearance as illustrated in FIGS. 1 and 2. To better appreciate what happens when the tissue protector 10 is in this unconstrained position deployed between the adjacent vertebrae, a handle 200 is illustrated in FIG. 8 having a spinal implant 100 positioned at a distal end of the handle 200 fixed at a proximal end of the implant 100 such that the implant 100 can be positioned onto the tissue protector 10 in the channel 16 between the enlarged ends 14 and slid into position. As shown, the tissue protector 10 provides at least one enlarged projection 14 to be adjacent or next to the nerve root and as long as the spinal implant maintains its position within the trough or channel 16 created by the two enlarged ends 14, the nerve root is protected. The implant 100 will slide freely into its desired implant location without any concern of hitting any nerve tissue or other tissue in the immediate area. This feature eliminates any risk of tissue or nerve tears.

While the implant 100 is shown on the flat web 12 of the body structure 11, it is appreciated that the spinal implant 100 similarly could be placed within the unconstrained first shapes of the other alternative embodiments having either a simple thin web 12 without any enlarged projections 14, shown in 6A, wherein the implant can be positioned inside the unconstrained first shape after the nerve shield 10 has been freed of the cannula 20 or similarly can be placed inside the other alternatives shown in FIG. 6C, 9A and 9C to allow the implant to be basically encapsulated by a tissue protector 10 as it is being passed through to its target location.

Alternatively, the implant can help or cause the tissue protector to achieve unconstrained final shape. So, as the implant advances, the tissue protector goes from constrained to unconstrained.

With reference to FIGS. 9A-9D, another alternative cross section is shown wherein the circular shape of 6A without any enlarged bulbous ends 14 is shown, however, in this case the web 12 has a somewhat "U" shape configuration that allows it to be rolled up and wrapped into a second tightly sized second shape to fit inside the cannula. This alternative embodiment similarly can have the enlarged bulbous ends 14 as previously discussed. However, in this shape, the unconstrained first shape of the device will take that approaching a "U" shaped central web 12. The alternatives provide a much deeper channel 16.

Figure 7A:
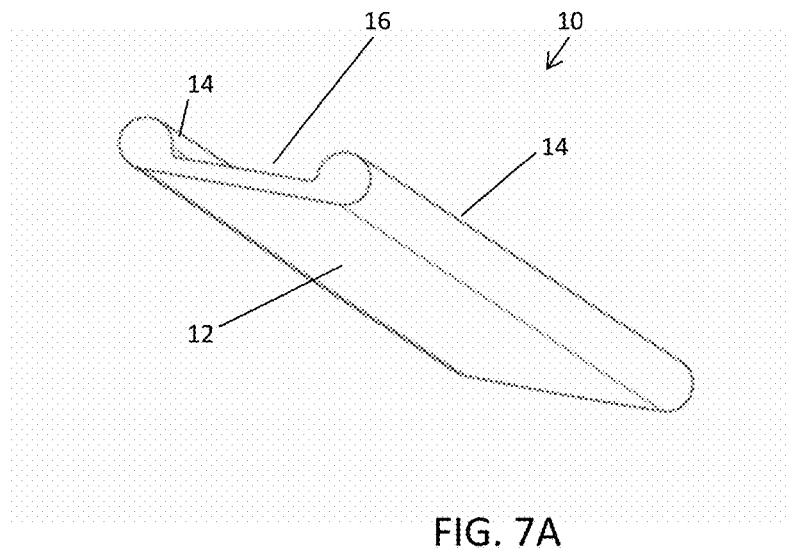
FIG. 7A is a solid version of the first embodiment FIG. 1.
Figure 7B:
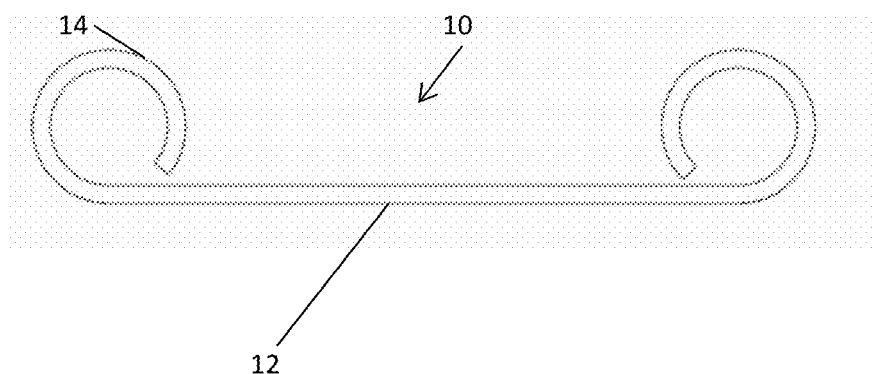
FIG. 7B is a rolled rails of the lateral ends version of the first embodiment of FIG. 1.

With reference to FIGS. 7A and 7B, the preferred embodiment shown in FIG. 1, can be formed as a solid piece of material molded or alternatively can be made from a thin piece of material having the ends rolled. When formed as a thin piece of material, it is likely that the material can be a thin nitinol or other thin metal material or any other material that can easily rolled into a tight configuration. As illustrated, the preferred embodiment achieves the shape somewhat similar to a partially unopened scroll and is commonly referred to as a scroll shield.

Since this is only one of the shapes that the tissue protector 10 can take, the alternative embodiments show variations in that shape. The thickness of the web 12 will be adapted to any size necessary to achieve an adequate wrapping. The primary objective is to ensure that the tissue protector 10 can be sufficiently constrained to fit easily and be held easily in a cannula 20 having an 8.5 mm diameter by way of example. Larger and smaller diameter cannulas could be used.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A tissue protector comprises:

a body structure having a first proximal end and a second distal end with a longitudinal extending thin flexible web with a pair of rigid or solid rails between said ends, the body structure having an unconstrained first shape with a length and a width configured to form the tissue protector, the body structure being a solid single piece of material compressible along the entire length of the web and configured to wrap or roll about a longitudinal axis of the body structure to a smaller constrained second shape sized to fit into a lumen of a cannula, the pair of rigid rails being longitudinal extending rails extending longitudinally along the length of web on each side of the web wherein the two rails of the body structure are parallel enlarged longitudinally extending projections extending the entire length of the body structure in both the constrained second shape and unconstrained first shape, the web having a constant width and being interposed between said parallel longitudinally extending rails to form a shallow channel extending the entire length from the first proximal end to the second distal end in the unconstrained first shape and wherein the body structure when placed inside the lumen of the cannula is configured to be positioned between two adjacent vertebral bodies and is configured to return to the unconstrained first shape when the cannula is withdrawn from between the two adjacent vertebral bodies while leaving the body structure between the two adjacent vertebral bodies, the web and the two rails are configured to shield a nerve root wherein the unconstrained first shape of the web is sized with the constant width to receive a spinal implant for insertion at the first proximal end in the shallow channel sliding along the web between the rigid rails to the second distal end between the two vertebral bodies as the web between the two rigid rails forms a guide for the spinal implant and a shield for the nerve root as the spinal implant is inserted.

2. The body structure of claim 1 wherein the second constrained shape is oval or round.

3. The tissue protector of claim 1 wherein the web has a thin oval or circular cross section in the unconstrained first shape.

4. The tissue protector of claim 1 wherein the web has a channel or "U" cross section in the unconstrained first shape.

5. The tissue protector of claim 1 wherein the rails when unconstrained have at least one rail configured to shield a nerve root.

6. The tissue protector of claim 1 wherein the rails are spaced by the web when the body structure is in the unconstrained first shape a lateral distance to receive a spinal implant.

7. The tissue protector of claim 6 wherein the pair of rails are configured to guide a spinal implant during insertion while at least one of said rails shields the nerve root.

8. The tissue protector of claim 7 wherein the rails of the body structure have a round or at least partially round cross section.

9. The tissue protector of claim 6 wherein the rails have a round or at least partially round cross section.

10. The tissue protector of claim 6 wherein the web has a thin rectangular cross section in the unconstrained first shape.

* * * * *